US00PP33197P3

(12) United States Plant Patent
Lavania et al.

(10) Patent No.: US PP33,197 P3
(45) Date of Patent: Jun. 22, 2021

(54) VETIVER PLANT NAMED 'CIMAP-FORAGIKA'

(50) Latin Name: ***Vetiveria* (syn. *Chrysopogon*) *zizanioides***
Varietal Denomination: CIMAP-FORAGIKA

(71) Applicant: COUNCIL OF SCIENTIFIC AND INDUSTRIAL RESEARCH, New Delhi (IN)

(72) Inventors: Umesh Chandra Lavania, Uttar Pradesh (IN); Seshu Lavania, Uttar Pradesh (IN); Vimala Yerramilli, Uttar Pradesh (IN); Basant Kumar Dubey, Uttar Pradesh (IN); Madhavi Singh, Uttar Pradesh (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/602,460

(22) Filed: Oct. 11, 2019

(65) Prior Publication Data

US 2021/0112694 P1 Apr. 15, 2021

(51) Int. Cl.
*A01H 5/12* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 5/00; A01H 5/12
See application file for complete search history.

*Primary Examiner* — Kent L Bell
(74) *Attorney, Agent, or Firm* — BakerHostetler

(57) ABSTRACT

The present invention relates to the development of a novel, morphologically and genetically distinct clone of vetiver [*Vetiveria zizaniodes* (L.) Nash. syn. *Chrysopogon zizanioides* (L.) Roberty; family Poacaeae] named 'CIMAP-FORAGIKA' that offers an ideal plant type to realize the twin application of Vetiver i.e. mitigation of soil erosion and landslides, as well as, a prospective forage in eco-plantations and cropping systems. This clone sports—(i) deep penetrating tufted roots coupled with profuse lateral secondary and tertiary roots that form an interwoven web of roots facilitating enhanced soil binding in landslide and erosion prone sites; and (ii) profuse shoot tillers bearing thinner leaves that have reduced (less) lignified tissue enabling leaf softness and palatability. The leaves of this clone are rich in protein (41 g/kg fresh weight) and crude fiber content (25 g/kg dry weight) but low in carbohydrates (31 g/kg dry weight), thus providing desirable digestibility and nutritional features. The clone has distinct morphological appearance differentiated by overall broader leaves (lamina width 12 mm compared to others ranging from 6.5 to 9 mm), lamina length 1.6 meter, and huge tiller production (>1.5 times) from amongst the other clones. The clone was identified as a natural variant occurring in a cultivated area having desired characteristics and was scored out from among the bulk of diverse wild collections. The identified clone is seed sterile i.e. a noninvasive feature necessary for global acceptance. This clone is characterized by a distinct DNA finger print, and can be asexually propagated for commercial plantation through slips (i.e. rooted tillers) arising from vegetative shoots.

4 Drawing Sheets

Specification includes a Sequence Listing.

Latin name of the genus and species of the plant claimed:

Latin name of the genus and species claimed: *Vetiveria* (syn. *Chrysopogon*) Species: *zizanioides*.

Variety denomination: 'CIMAP-FORAGIKA'.

BACKGROUND OF THE INVENTION

Vetiver, *Vetiveria zizanioides* (L.) Nash. (*Chrysopogon zizanioides* L. Roberty), a C4 plant has been nicknamed as miracle grass that can grow under drought/stress, water logging, 4-11 pH, sewage/waste water, and can thrive under temperature conditions ranging from 5-50° C. Its roots are valued for perfumery oil since ancient times; and hedges for contour protection. Organized cultivation of vetiver has been in practice since 1940s in southern states of India, although its collection from wild has been there since centuries in northern states of the country for its aromatic roots, and root oil considered as perfume in its own right (Lavania UC, 2003; Lavania , 2008). Vetiver root oil is accumulated in the innermost cortical cell layers adjoining endodermis and also in the lysigenous aerenchyma in naturally grown plants. Lately, vetiver has been extensively utilized for its multifarious environmental applications in over 100 countries, mainly for soil and slope stabilization owing to its vertically growing deep penetrating web forming root growth pattern (Lavania 2008; Banerjee et al.; 2019). Further, vetiver grass model has been considered as a potential green resource for sequestration of atmospheric carbon into subsoil likened to trees (Lavania UC & Lavania, S., 2009). Also, young shoots of vetiver grass are considered to have the qualities of edible herbage that may be used as ruminant feed if mixed with other good quality feed and forages (Lukiwati, 2015). India is considered as the centre of origin and dispersion of this miracle grass (Lavania, 2002, 2008). Two diverse geographic complexes are known to be occurring in India: (i) the north Indian type characterized by profuse flowering seed forming types that sports thick but smooth roots with low content of essential oil, and (ii) south Indian type characterized by low/late flowering and low seed forming types that sports thin but more roots with relatively higher concentration of essential oil (Lavania, 2008). Extensive transcriptome analysis has further confirmed that the two types are distinctly different for their genetic background (Chakrabarty et al.; 2015). Being the native home of vetiver, India is enriched with repertoire of genetic diversity for morphotypic, reproductive, histological and physiological features. As such India offers opportunities to score vetiver plant type/s for specific industrial and/or environmental applications. Lavania, S (2003, 2019) has in fact emphasized the need to identify utility specific plant types and had underpinned ideal root characteristics for specific applications. However, no variety or genotype has yet been identified that combines the twin features of an ideal soil binder as well as the required qualities of forage plant—so necessary for sustainability of ecological plantations. The present invention i.e. 'CIMAP-FORAGIKA', overcomes this problem to a large extent as this plant offers better soil binding features on account of presence of profuse secondary and tertiary roots that facilitate enhanced soil binding property and at the same time providing palatable nutritious shoots for grazing as forage for sustained utilization along the landslide and erosion prone natural sites and habitats.

BRIEF SUMMARY OF THE INVENTION

The present invention relates to the development of a seed-sterile novel and distinct plant type (clone) of vetiver *Chrysopogon zizanioides* sporting profuse tillering, soft palatable leaves rich in crude fiber suitable as cattle fodder, and deep penetrating tufted roots coupled with secondary and tertiary roots ideal for soil binding of degraded soil in erosion and landslide prone sites. This clone was found in cultivated planes of district Mathura of the state of Uttar Pradesh, India, located at the latitude −27.4, longitude 77.6, gps coordinate 27° 29'32 N and 77° 40'25 E along the left bank of river Yamuna in its catchment area. This clone was isolated after scoring diverse collections obtained from natural populations found in cultivated area for desirable features viz. asexual reproduction, seed sterility to realize non-invasiveness necessary in ecological plantations, fast growth and palatable quality of above ground part meeting forage characteristics, and deep penetrating root system sported with profuse secondary/tertiary roots to realize high web-forming features enabling enhanced soil binding potential. This plant named 'CIMAP-FORAGIKA' as illustrated and described herein is a genetically uniform and stable new and distinct variety of diploid (2n=20) of *Vetiveria zizanioides* (L.) Nash. syn. *Chrysopogon zizanioides* (L.) Roberty), that could be asexually propagated through vegetative slips (tillers) arising from the shoot base. The clone is suitable in ecological plantations as hedge rows to mitigate soil erosion/landslides along hills, pastures, slopes, contours of water bodies, and at the same time serving as forage for grazing animals for natural and sustained maintenance of plantations. The leaves of this clone are rich in protein (41 g/kg fresh weight) and crude fiber content (25 g/kg dry weight) but low in carbohydrates (31 g/kg dry weight), thus providing desirable digestibility and nutritional features. The clone has distinct morphological appearance differentiated by overall broader leaves (lamina width 12 mm compared to others ranging from 6.5 to 9 mm), lamina length 1.6 meter, and huge tiller production (>1.5 times), profuse secondary and tertiary roots (>2.5 times), from amongst the other clones. The usability of above ground part as forage and underground part (root system) for soil binding/mitigation of soil erosion and long term carbon sequestration, coupled with environment friendly non-invasive features are the unique qualities of the instant clone that are efficiently combined in one plant type. This has not been reported earlier in any other variety or genotype known to the inventors. The instant clone is a perennial plant type and could be obtained for public use in Lucknow, India.

Primary objective of this invention was to develop a noninvasive plant type of Vetiver grass for ecological plantations that combines twin features in its root and shoot i.e. (i) roots with physical characteristics that adds value to its soil binding property to realize enhanced stabilization of degraded soil/slopes, and (ii) shoots that are nutritious and palatable thus suitable as fodder for grazing, enabling natural sustainability of such plantations. No such ideal plant type has hitherto been made available, and the development of the vetiver plant named 'CIMAP-FORAGIKA' fills this gap. The instant clone is ideally suitable for plantations along the erosion/landslide prone slopes to mitigate landslide and soil degradation in a sustainable manner.

BRIEF DESCRIPTION OF THE ACCOMPANYING DRAWINGS

FIG. 1. Fully grown-up plant, leaf width and root pattern of Clone 'CIM-VRIDDHI': (left) vs Clone 'CIMAP-FORAGIKA' (right). Note high tiller and drooping and broad leaves, and profuse secondary roots in the clone 'CIMAP-FORAGIKA'.

FIG. 2. Root pattern of 'CIMAP-FORAGIKA': Left—under field conditions, Right—under experimental conditions grown in microcosm. Note profuse primary, secondary and tertiary roots.

FIG. 3. Characterization of clone 'CIMAP-FORAGIKA': A . Floral organs, B. ISSR DNA finger print (M—Marker, and 1-10 ISSR primers—as per sequence details given).

FIG. 4. Depiction of micromorphological features (Inflorescence, pollen grains, pistil, essential oil secretary cell i.e. eo and TS of leaf) showing comparison between Clone 'CIM-VRIDDHI' (A,B,C, G,I) and 'CIMAP-FORAGIKA' (D,E,F, H, J). Note—low essential oil cells (eo), reduced leaf thickness in Clone 'CIMAP-FORAGIKA'.

DETAILED BOTANICAL DESCRIPTION

Breeding History: Owing to historical importance and demand of vetiver oil in aroma industry several improved varieties of vetiver grass have been developed in India (Lavania 2008). Also, some ecotypes have been identified in Thailand for its utility in environmental conservation. Two novel clones of Vetiver, namely 'CIMAP-KH40'—U.S. Plant Pat. No. 26,474 and 'CIMAP-Khushinolika'—U.S. Plant Pat. No. 28,388 have been developed for application for Carbon sequestration/soil conservation, and specific quality of essential oil, respectively. Although, there are indications that cattle can feed on young shoots (Lukiwati, 2015), but no effort has been made to develop/identify a suitable clone for utilization as a forage material. The present invention was therefore intended to develop a clone for ecological plantations that combines twin features of vetiver grass for stabilization of degraded soil/slopes as well as to serve as a fodder for grazing animals onsite for sustainability of such plantations along the degrading lands, slopes, hills. The development of the present clone fills this gap.

Method of Development of the Plant Clone 'CIMAP-FORAGIKA': India is the centre of origin and dispersion of Vetiver. The plant has its natural presence across India inhabiting diverse habitats in wild state enriched with repertoire of morphogenetic, structural, reproductive and physiological diversity. An intensive programme was undertaken to identify a desired plant type from among the collections made from natural populations occurring in the cultivated area. A large number of Vetiver plants and seeds were collected from the wild habitats spread across the agricultural plains/river banks and terai regions of Uttar Pradesh, and certain areas of Maharashtra (Kolhapur), Karnataka (Bengaluru) and Tamilnadu (Chennai), and grown at the experimental farm in Lucknow, India, for their first look at their growth behavior and external morphology with a primary focus on fast growth/high tillering and low seed set. Twelve clones thus screened out were further screened out for root growth behavior with a focus on presence of secondary/tertiary roots and low oil, broader leaves with thin lamina and low seed set under field conditions. Side by side these clones were histologically examined for frequency of occurrence of essential oils secretary cells in the roots in six month aged roots, cortex/steel ratio, leaf lamina for thickness of leaf sclerenchyma, seed set and seed fertility. Out of these six morphologically diverse clones that promise high shoot biomass, broad and soft textured leaves and fast growing high number of roots were identified for further performance and growth behavior under field conditions to identify a clone of choice. The clone 'CIMAP-FORAGIKA' thus identified was further tested for its biological attributes and performance vis-à-vis other standard clones earlier released for industrial and environmental applications in a microcosm module to record empirical data on various morphological, reproductive, anatomical, physiological and nutrition quality parameters; the details of which are given in Tables 1 and 2, and also depicted by way of figures (FIG. 1-4).

Nutritional quality of vetiver leaves: One of the important objectives of the present study was to identify a vetiver clone that can also be used as a fodder for cattle in ecological plantations. Accordingly, while selecting the clones a due emphasis was laid that the clone to be selected should have softer leaves for easy digestibility combined with good nutritional quality. The selected clones were subjected to nutritional analysis vis-à-vis other improved varieties. The data thus obtained is given below in the Table 2.

TABLE 1

Comparison of Description of morphometric, histological and physiological features of clone 'CIMAP-FORAGIKA', vis-à-vis other developed varieties.

| Characteristics | 'CIMAP-FORAGIKA' | 'CIM-VRIDDHI' | 'CIMAP-KH40' |
|---|---|---|---|
| General morphology | Very broad and soft leaf, high tillering and profuse secondary/tertiary roots | Profuse flowering, low seed set, and smooth roots | Low and late flowering, broad leaf, non-seeding, thick and smooth roots |
| Growth Habit | Fast growing, profuse tillering | Fast growing | Slow growing |

TABLE 1-continued

Comparison of Description of morphometric, histological and physiological features of clone 'CIMAP-FORAGIKA', vis-à-vis other developed varieties.

| | | | |
|---|---|---|---|
| Plant height in cms (taken as leaf length) | 164 | 168 | 142 |
| Shoot yield (culm/leaf dry matter) after 5 months | 120 g | 85 g | 95 g |
| Carbon content in shoots (%) | 37 | 36 | 38 |
| Number of leaves/tiller | 7-9 | 6-9 | 7-9 |
| Number of slip/tillers after 5 months/12 months | 25-28/47-50 | 20-23/28-35 | 18-20/32-38 |
| Inflorescence stalk length in cms (culm and inflorescence combined) | 230 | 235 | 190 |
| Culm length (cms) | 136 | 140 | 95 |
| Leaf color | RHS 143B Green | RHS 137 A Green | RHS 138B Green |
| Leaf Texture/No. of air chambers | Smooth/24-26 | Stiff/20-22 | Stiff/20-22 |
| Leaf cuticle thickness (mm) Adaxial/abaxial | 0.0037/0.0037 | 0.0037/0.0055 | 0.0038/0.0050 |
| Leaf Thickness at midrib (mm) | 0.418 | 0.45 | 0.66 |
| Vascular tissue thickness at mid rib (mm) | 0.138 | 0.18 | 0.25 |
| Leaf Width (mm) | 12.0 | 8.0 | 6.5 |
| Sclerenchyma thickness (mm) | 0.055 | 0.070 | 0.057 |
| Leaf Sclerenchyma | 12.43% | 13.62% | 16.42% |
| Leaf blade stomatal index | 7.57 | 7.62 | 6.47 |
| Leaf base stomatal index | 2.25 | 2.93 | 1.52 |
| Average size of guard cell | 116 $\mu m^2$ | 75 $\mu m^2$ | 119 $\mu m^2$ |
| No. of Stomata/$mm^2$ | 197 | 181 | 77 |
| Seed set and germination | 00% | 2-3% | 0.8-1.0% |
| Number of primary roots after 5 months | 223 | 193 | 208 |
| Root Length (cm) after 5 months | 135-160 | 150-155 | 153-185 |
| No. of Primary roots per tiller | 12-25 | 10-18 | 8-18 |
| No. of Secondary roots/2.5 Cms | 25-55 | 12-22 | 8-18 |
| No. of Tertiary roots/2.5 Cms | 27-45 | 11-17 | 10-18 |
| Average root diameter/stele diameter (at the base of main root) mm | 1.84/0.86 | 2.1/1.11 | 2.49/1.53 |
| Total root dry weight (g/plant) after 5 months | 40 g | 38 g | 43 g |
| Carbon content in Roots (%) | 44 | 42 | 43 |
| Oil Content (%) in fresh roots) at one year | 0.3 | 1.0 | 0.7 |
| Photosynthesis efficiency i.e. $CO_2$ exchange rate at 10-15 $\mu mol/m^2$/sec photosynthetic active radiation | 5.46/$m^2$/sec | 4.44/$m^2$/sec | 7.634 $\mu mol/m^2$/sec |
| Chlorophyll content | 2.186 µg/g fresh wt. | 2.336 µg/g fresh wt. | 2.386 µg/g fresh wt. |

TABLE 1-continued

Comparison of Description of morphometric, histological and physiological features of clone 'CIMAP-FORAGIKA', vis-à-vis other developed varieties.

| | | | |
|---|---|---|---|
| Cytological differentiation | 2n = 20 | 2n = 20 | 2n = 20 |
| Range in Chromosome size | 2.0 to 4.0 μm | 2.1 to 4.0 μm | 2.1 to 4.4 μm |
| Haploid chromatin length | 28 μm | 28 μm | 29 μm |

| Characteristics | 'CHIANG RAI' | 'CIMAP-KHUSI-NOLIKA' |
|---|---|---|
| General morphology | Semi-Spreading, low flowering, smooth and thin roots | Dwarf, spreading type canopy, late and low flowering, smooth and thin roots |
| Growth Habit | Medium growing | Fast growing |
| Plant height in cms (taken as leaf length) | 145 | 141 |
| Shoot yield (culm/leaf dry matter) after 5 months | 65 g | 75 g |
| Carbon content in shoots (%) | 37 | 36 |
| Number of leaves/tiller | 8-11 | 7-9 |
| Number of slip/tillers after 5 months/12 months | 25-28/40-44 | 22-24/30-34 |
| Inflorescence stalk length in cms (culm and inflorescence combined) | 245 | 197 |
| Culm length (cms) | 128 | 127 |
| Leaf color | RHS 137 B Green | RHS 137 B Green |
| Leaf Texture/No. of air chambers | Stiff/24-26 | Stiff/20-22 |
| Leaf cuticle thickness (mm) Adaxial/abaxial | 0.0041/0.0048 | 0.0048/0.0048 |
| Leaf Thickness at midrib (mm) | 0.35 | 0.54 |
| Vascular tissue thickness at mid rib (mm) | 0.125 | 0.115 |
| Leaf Width (mm) | 9.0 | 8.0 |
| Sclerenchyma thickness (mm) | 0.060 | 0.062 |
| Leaf Sclerenchyma | 15.05% | 11.4% |
| Leaf blade stomatal index | 7.39 | 9.04 |
| Leaf base stomatal index | 1.62 | 2.5 |
| Average size of guard cell | 103 $\mu m^2$ | 81 $\mu m^2$ |
| No. of Stomata/$mm^2$ | 199 | 255 |
| Seed set and germination | 8-10% | 8-11% |
| Number of primary roots after 5 months | 198 | 195 |
| Root Length (cm) after 5 months | 130-140 | 125-135 |
| No. of Primary roots per tiller | 12-20 | 10-23 |
| No. of Secondary roots/2.5 Cms | 12-18 | 12-20 |
| No. of Tertiary roots/2.5 Cms | 12-18 | 15-24 |

TABLE 1-continued

Comparison of Description of morphometric, histological and physiological features of clone 'CIMAP-FORAGIKA', vis-à-vis other developed varieties.

| | | |
|---|---|---|
| Average root diameter/stele diameter (at the base of main root) mm | 1.9/1.4 | 1.75/0.9 |
| Total root dry weight (g/plant) after 5 months | 31 g | 37 g |
| Carbon content in Roots (%) | 42 | 44 |
| Oil Content (%) in fresh roots) at one year | 0.8 | 1.0 |
| Photosynthesis efficiency i.e. $CO_2$ exchange rate at 10-15 μmol/$m^2$/sec photosynthetic active radiation | 5.49/$m^2$/sec | 5.12/$m^2$/sec |
| Chlorophyll content | 2.376 μg/g fresh wt. | 2.343 μg/g fresh wt. |
| Cytological differentiation | 2n = 20 | 2n = 20 |
| Range in Chromosome size | 2.1 to 4.2 μm | 1.9 to 4.0 μm |
| Haploid chromatin length | 29 μm | 8 μm |

TABLE 2

Nutritional characteristics of various vetiver clones based on biochemical analysis of leaves at two/three months of growth after planting*.

| CLONE SAMPLE | N | Pro-teins | Carbo-hydrates | P | Crude fibre |
|---|---|---|---|---|---|
| at 2 months | | | | | |
| 'CHIANG RAI' | 14.11 | 30.29 | 59.58 | 21.85 | 0.218 |
| 'CIMAP-FORAGIKA' | 6.6 | 36.03 | 32.13 | 29.78 | 0.205 |
| 'CIM-VRIDDHI' | 7.37 | 29.64 | 143.8 | 48.64 | 0.154 |
| 'CIMAP-KH40' | 5.9 | 29.54 | 159.17 | 35.19 | 0.172 |
| 'CIMPA-KHUSHINOLIKA. | 2.92 | 47.38 | 91.61 | 54.39 | 0.19 |
| at 3 months | | | | | |
| 'CHIANG RAI' | 12.14 | 38.18 | 31.47 | 55.89 | 0.163 |
| 'CIMAP-FORAGIKA' | 3.77 | 41.17 | 31.15 | 26.22 | 0.244 |
| 'CIM-VRIDDHI' | 3.99 | 27.19 | 138.53 | 41.74 | 0.206 |
| 'CIMAP-KH40' | 4.26 | 29.64 | 198.11 | 40.59 | 0.229 |
| 'CIMAP-KHUSHINOLIKA' | 3.51 | 48.46 | 100.86 | 41.74 | 0.197 |

| CLONE SAMPLE | Fe | Cu | Zn | Ca | K | Na |
|---|---|---|---|---|---|---|
| at 2 months | | | | | | |
| 'CHIANG RAI' | 216.03 | 0.024 | 5.346 | 21 | 85 | 12 |
| 'CIMAP-FORAGIKA' | 262.1 | 0.031 | 6.048 | 17 | 197 | 7 |
| 'CIM-VRIDDHI' | 262.82 | 0.033 | 7.112 | 21 | 191 | 12 |
| 'CIMAP-KH40' | 334.25 | 0.03 | 4.751 | 18 | 111 | 7 |
| 'CIMPA-KHUSHINOLIKA. | 157.46 | 0.022 | 5.559 | 22 | 181 | 15 |
| at 3 months | | | | | | |
| 'CHIANG RAI' | 218.00 | 0.026 | 5.349 | 23 | 115 | 45 |
| 'CIMAP-FORAGIKA' | 263.00 | 0.032 | 6.049 | 22 | 45 | 21 |
| 'CIM-VRIDDHI' | 262.98 | 0.032 | 7.114 | 42 | 161 | 22 |

TABLE 2-continued

Nutritional characteristics of various vetiver clones based on biochemical analysis of leaves at two/three months of growth after planting*.

| | | | | | | |
|---|---|---|---|---|---|---|
| 'CIMAP-KH40' | 336.30 | 0.031 | 4.750 | 19 | 103 | 19 |
| 'CIMAP-KHUSHINOLIKA' | 156.00 | 0.022 | 5.561 | 21 | 58 | 34 |

*Estimated values measures as: N, Carbohydrate, P and Crude fibre as mg/gm dry weight, Protein taken as mg/gm fresh weight, K, Na, Fe, Cu, Zn as ppm/25 mg dry weight.

The leaves of the clone 'CIMAP-FORAGIKA' are enriched with protein (41 g/kg fresh weight), crude fiber content (25 g/kg dry weight), but low in carbohydrates (31 g/kg dry weight), alongwith desirable amount of essential minerals. The presence of given amount of fiber content makes it digestible by the cattle, and the protein content adds to its nutritional quality thus making it suitable as a forage. Thus it is inferred that the Clone 'CIMAP FORAGIKA' besides being suitable for soil conservation, is high in crude fibre content and contains reasonable amount of protein. It has low Ca and Na levels in the leaves but high level of potassium to tone up metabolism. July to October and February to May are favourable for growth and useful for consumption. Presence of moderate Fe, Cu and Zn levels keep major synthetic pathways to function harmoniously.

BOTANICAL DESCRIPTION AND CHARACTERIZATION

The new and distinct clone of *Chrysopogon zizanioides* 'CIMAP-FORAGIKA' is suitable for ecological plantations as hedge rows for soil/slope stabilization along pastures, landslide/mudslide prone foothills; contour protection of river banks, ponds/bunds, on account of its massive web-forming roots that facilitate soil binding, and at the same time promising sustainability of such plantations on account of grazing that facilitates its continued rejuvenation. Further, since this clone is seed sterile therefore any such plantation does not pose any threat of getting invasive/weedy.

Uniformity and stability: The given plant is a seed sterile clone that could propagate only vegetatively promising uniformity. Its stability has been tested and ensured through several multiplication cycles over five years at the experimental farm at Lucknow, India. The clone could be easily propagated asexually through slips (tillers) arising from vegetative shoot to generate planting material.

Flowering behavior: Although, this clone flowers as usual, but the pollen born are sterile and the seeds formed are empty/sterile and does not germinate at all.

Growth behavior and root pattern: The plant is quite distinct in its growth behavior, sporting profuse tillering i.e. >1.5 times compared to others, and its roots bear huge secondary and tertiary roots far more (>2.5 times) compared to all other clones as well as those occurring in the natural habitats known to the inventors. Its leaves are quite broad but thin (less lignified) compared to others known to the inventors.

Nutritional quality: This clone is rich in crude fiber enabling its easy digestibility, and presence of moderate Fe, Cu and Zn levels keep major synthetic pathways to function harmoniously.

Essential oil secretary cells: The number and volume of oil secretary cells is quite low, and so does the essential content (0.3%) far below than the other cultivated varieties. Therefore, this plant is quite ideal for ecological plantations since this will not attract the root diggers that wish to uproot the plant for its aromatic roots.

Morphological characterization:

*Genus.*—*Vetiveria* (syn. *Chrysopogon*).

*Species.*—*Zizanioides.*

*Family.*—Poaceae.

*Common name.*—Vetiver, Khus (in Hindi in India).

*Cultivar name.*—('CIMAP-FORAGIKA'). It is a fast growing profuse tillering diploid (2n=20), normal flowering clone, but the seed borne are sterile that do not germinate. Its roots sport huge secondary and tertiary roots that enhance its soil binding potential, it is fast growing with profuse tillering capacity (>1.5 times compared to other clones), leaves are broad, palatable, soft with less lignified tissue meeting the qualities desired in a forage.

Morphometric description of the clone 'CIMAP-FORAGIKA':

*General morphology.*—Profuse tillering semi-spreading type above-ground canopy with tufted roots with profuse secondary and tertiary roots, late (at 18-20 months after initial planting) but prolonged flowering lasting over three months from October to December (cf. other north Indian genotypes flower for over two months from June to September). Short and compact panicle, broader and somewhat drooping leaves with less intense leaf color are other general appearance feature that distinguishes this plant type from other vetiver genotypes.

*Plant height.*—1.8 to 2.1 m.

*Plant canopy.*—Semi-spreading, diameter 80 to 100 cms.

*Growth habit.*—Fast growing, profuse tillering, flowering is initiated in October (FIG. 1).

*Branching.*—Tillers.

*Culms.*—Compressed and well defined solid nodes and internodes.

*Number of tillers.*—35 to 45 after six months (cf. 26-32 in standard check).

*Number of nodes in a tiller.*—9-12.

*Average culm length.*—2.12 m (cf. 2.45 m in standard check).

*Leaf margin and texture.*—Serrate, dorsal surface rough, ventral glabrous and rough along the edges, ligule fine hairy ring and auricle absent.

*Leaf length.*—110 m to 130 m.

*Leaf width.*—12 mm to 14 mm.

*Lamina colour.*—(The Royal Horticultural Society Colour Chart (R.H.S. Colour Chart), Royal Horticultural Society London, $5^{th}$ edition 2007) RHS Green group — upper (143B), lower (143A).

*Leaf sheath keeled, colour.*—RHS Yellow green group (145-C).

*Leaf tip.*—Acute.

*Stomata.*—Lamina stomatal Index 7.6; size of stomatal complex and stomatal guard cell 520 $\mu m^2$ and 116 $\mu m^2$ respectively (compared to 870 $\mu m^2$ and 80-100 $\mu m^2$ in standard check).

*Inflorescence.*—Panicle. Length of the flowering shoot, length of panicle bearing peduncle, length of spike bearing part of peduncle, number of spike bearing nodes in a peduncle, number of spikes per node, number of florets (diad) per spike rachilla (diad i.e. a pair of sessile and pedicellate spikelet), respectively are 235 cms, 35 cms, 25 cms, 16 spikes bearing nodes in a peduncle, 6 spikes per node, and 8 florets (diad) per spike rachilla compared to standard check respectively 245 cms, 90 cms, 38 cms, 9 spikes bearing nodes in a peduncle, 17 spikes per node, and 9 florets (diad) per spike rachilla.

*Inflorescence colour*.—Color of peduncle axis — RHS color — Green yellow group 154D (cf. standard check Grey Red group 182 B), Color of Lemma — RHS color — Grey green 190C, Stigma feathery with RHS color — Purple violet N81A (cf. standard check that has RHS-Grey purple group 183A).

*Flower*.—Spikelet (diad) borne in pair of sessile (hermaphrodite) and pedicelled (staminate or empty) having Glume (enclosing flower) length of 3.0 mm and 2.4 mm respectively, compared to 3.6 mm and 3.1 mm in the standard control.

*Glume*.—RHS color yellow — Greyed purple 183A with base and spines Red-Purple Group 72A, coriaceous, Lower glume — ovate with margins ciliated and inflexed, 3.37×0.5 mm in the middle/Upper glume — elliptic with margin ciliated and inflexed, 3.48×0.9 mm in the middle.

*Lemma*.—Lower lemma (RHS color — Grey white group 156 B) membranous, obovate, 3.4×1.26 mm in middle; Upper lemma (RHS color — White-Grey 155B), hyaline, oblong acuminate with awn, 3.57×0.78 mm in middle.

*Palea*.—RHS color — White Group NN155D, hyaline, oblong, 2.01×0.57 mm in the middle, apex obtuse and ciliated.

*Stigma*.—Feathery (usually with two feathers, but three feathers is also in common occurrence) with RHS color — Purple violet N81A.

*Flowering*.—Late flowering (in October under Lucknow conditions) compared to standard flowering in May and June.

*Seed*.—RHS color — Greyed-Yellow Group 162 B, Oblong with obtuse tip, length 1.63 mm (cf. 1.8-2.00 mm in standard).

*Root*.—Diameter near the root base 2.0 mm, sported with profuse secondary/tertiary roots.

*Essential oil*.—Content — low (<0.3%) in fresh roots with 46% moisture at one year, Odor — earthy note, Color — light yellow (RHS Color — Greyed Yellow 162 A), Refractive index — 1.519, Optical rotation [α] — 34.8.

DISTINGUISHING FEATURES AND ADVANTAGES OF THE CLONE 'CIMAP-FORAGIKA'

Compared to all other varieties of vetiver, the said clone 'CIMAP-FORAGIKA' is distinct in respect of combination of characters like: fast growth, profuse tillers, soft but broader forage quality leaves, late but long flowering, compact inflorescence with short panicle, smaller floret and seed size, sterile seed, tufted roots sported with profuse secondary and tertiary roots and low oil content, and characteristic ISSR-DNA fingerprints. The clone offers the following distinct advantages over other existing clones/varieties of vetiver:

(i) This clone offers a novel combinations of a forage grass and soil binder suitable for ecological plantations along the degraded lands, slopes, foot hills and mudslide prone sites.

(ii) Owing to profuse secondary and tertiary roots this clone offers better soil binding property and therefore enhanced potential to help mitigate soil erosion/landslides along hills, pastures, slopes, soil bunds/contours of water bodies, river banks as hedge rows.

(iii) At the same time, its nutritious and soft palatable leaves/shoots could serve as forage for grazing animals on site. Such grazing facilitates natural rejuvenation of plantations to realize sustainability.

(iv) In addition to its potential as a soil binder and forage, this clone could sequester about 800 g of carbon per meter squire per year in subsoil horizon.

(v) The clone is suitable for ecological plantations on account of its noninvasive feature (its seeds are sterile) and low oil in roots (that works as a deterrent to root diggers) promising no threat of becoming weedy or uprooting by human intervention.

DISTINCTIVENESS OF THE PLANT THROUGH IISR FINGERPRINTS

DNA Fingerprints of clone 'CIMAP-FORAGIKA' based on ISSR markers

FIG. 2

```
SEQUENCE LISTING of ISSR markers used
Sequence ID No. 1
Length: 17
Type: DNA
Organism: ARTIFICIAL SEQ
Other Information: ISSR PRIMER UBC 807
SEQUENCE: agagagagag agagagt

Sequence ID No. 2
Length: 17
Type: DNA
Organism: ARTIFICIAL SEQ: ISSR PRIMER
Other Information: ISSR PRIMER UBC 810
SEQUENCE: gagagagaga gagagat

Sequence ID No. 3
Length: 17
Type: DNA
Organism:ARTIFICIAL SEQ: ISSR PRIMER
Other Information: ISSR PRIMER UBC 811
SEQUENCE: gagagagaga gagagac

Sequence ID No. 4
Length: 17
Type: DNA
Organism: ARTIFICIAL SEQ: ISSR PRIMER
Other Information: ISSR PRIMER UBC 812
SEQUENCE: gagagagaga gagagaa

Sequence ID No. 5
Length: 17
Type: DNA
Organism: ARTIFICIAL SEQ: ISSR PRIMER
Other Information: ISSR PRIMER UBC 814
SEQUENCE: ctctctctct ctctcta

Sequence ID No. 6
Length: 17
Type: DNA
Organism: ARTIFICIAL SEQ: ISSR PRIMER
Other Information: ISSR PRIMER UBC 818
SEQUENCE: cacacacaca cacacag

Sequence ID No. 7
Length: 17
Type: DNA
Organism: ARTIFICIAL SEQ: ISSR PRIMER
Other Information: ISSR PRIMER UBC 823
```

-continued

SEQUENCE: tctctctctc tctctcc

Sequence ID No. 8
Length: 17
Type: DNA
Organism: ARTIFICIAL SEQ: ISSR PRIMER
Other Information: ISSR PRIMER UBC 825
SEQUENCE: acacacacac acacact Sequence ID No. 9
Length: 17

-continued

Type: DNA
Organism: ARTIFICIAL SEQ: ISSR PRIMER
Other Information: ISSR PRIMER UBC 826
SEQUENCE: acacacacac acacacc Sequence ID No. 10
Length: 17
Type: DNA
Organism: ARTIFICIAL SEQ: ISSR PRIMER
Other Information: ISSR PRIMER UBC 828
SEQUENCE: tgtgtgtgtg tgtgtga

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: ISSR PRIMER UBC 807

<400> SEQUENCE: 1 agagagagag agagagt 17

<210> SEQ ID NO 2
<211> LENGTH: 17
<212> TYPE: DNA
<213> ORGANISM: Artificial Sequence
<220> FEATURE:
<223> OTHER INFORMATION: ISSR PRIMER UBC 810

<400> SEQUENCE: 2 gagagagaga gagagat 17

<210> SEQ ID NO 3
<211> LENGTH: 17
<212> TYPE: DNA
<213> ORGANISM: Artificial Sequence
<220> FEATURE:
<223> OTHER INFORMATION: ISSR PRIMER UBC 811

<400> SEQUENCE: 3 gagagagaga gagagac 17

<210> SEQ ID NO 4
<211> LENGTH: 17
<212> TYPE: DNA
<213> ORGANISM: Artificial Sequence
<220> FEATURE:
<223> OTHER INFORMATION: ISSR PRIMER UBC 812

<400> SEQUENCE: 4 gagagagaga gagagaa 17

<210> SEQ ID NO 5
<211> LENGTH: 17
<212> TYPE: DNA
<213> ORGANISM: Artificial Sequence
<220> FEATURE:
<223> OTHER INFORMATION: ISSR PRIMER UBC 814

<400> SEQUENCE: 5 ctctctctct ctctcta 17

-continued

```
<210> SEQ ID NO 6
<211> LENGTH: 17
<212> TYPE: DNA
<213> ORGANISM: Artificial Sequence
<220> FEATURE:
<223> OTHER INFORMATION: ISSR PRIMER  UBC 818

<400> SEQUENCE: 6

cacacacaca cacacag                                                  17


<210> SEQ ID NO 7
<211> LENGTH: 17
<212> TYPE: DNA
<213> ORGANISM: Artificial Sequence
<220> FEATURE:
<223> OTHER INFORMATION: ISSR PRIMER  UBC 823

<400> SEQUENCE: 7

tctctctctc tctctcc                                                  17


<210> SEQ ID NO 8
<211> LENGTH: 17
<212> TYPE: DNA
<213> ORGANISM: Artificial Sequence
<220> FEATURE:
<223> OTHER INFORMATION: ISSR PRIMER  UBC 825

<400> SEQUENCE: 8

acacacacac acacact                                                  17


<210> SEQ ID NO 9
<211> LENGTH: 17
<212> TYPE: DNA
<213> ORGANISM: Artificial Sequence
<220> FEATURE:
<223> OTHER INFORMATION: ISSR PRIMER  UBC 826

<400> SEQUENCE: 9

acacacacac acacacc                                                  17


<210> SEQ ID NO 10
<211> LENGTH: 17
<212> TYPE: DNA
<213> ORGANISM: Artificial Sequence
<220> FEATURE:
<223> OTHER INFORMATION: ISSR PRIMER  UBC 828

<400> SEQUENCE: 10

tgtgtgtgtg tgtgtga                                                  17
```

What is claimed is:

1. A new and distinct variety of Vetiver plant named ‘CIMAP-FORAGIKA’ as described and illustrated.

* * * * *

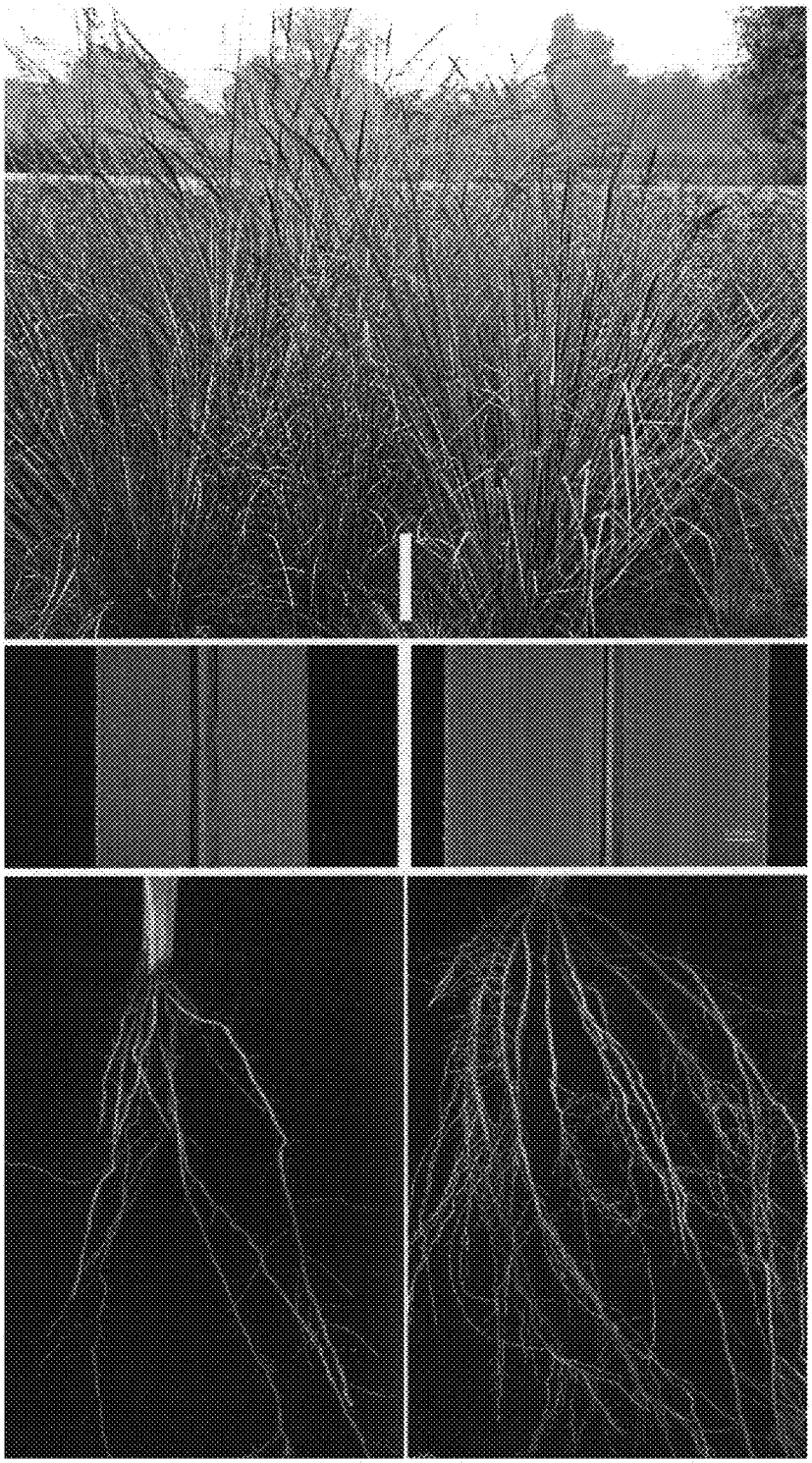
Figure 1. Fully grown-up plant, leaf width and root pattern of Clone CIM-VRIDDHI (left) vs Clone CIMAP-FORAGIKA (right) .Note high tiller and drooping and broad leaves , and profuse secondary roots in the clone CIMAP-FORAGIKA

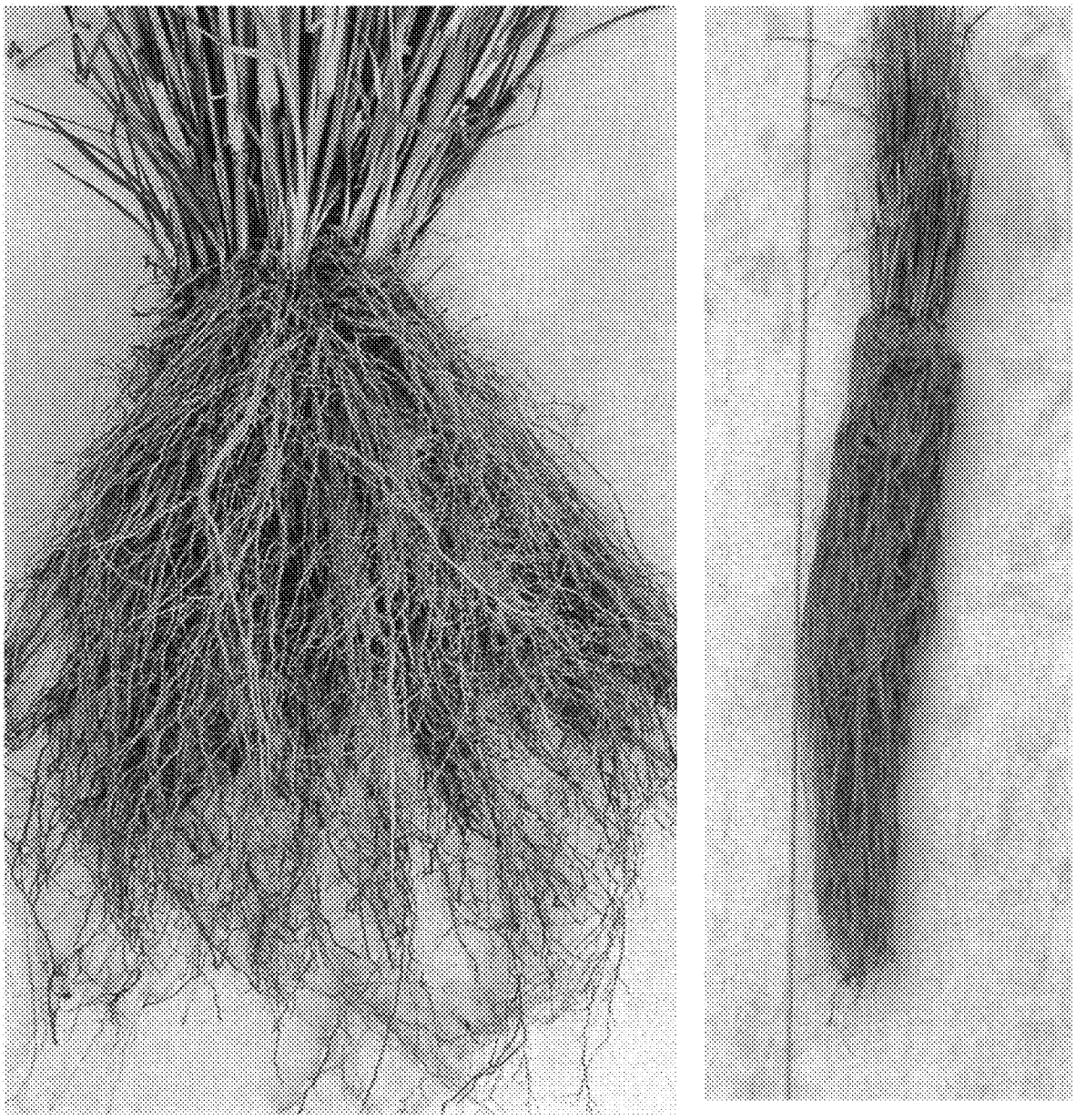
Figure 2. Root pattern of CIMAP-FORAGIKA.
Left – under field conditions, Right – under experimental conditions grown in microcosm. Note profuse primary, secondary and tertiary roots.

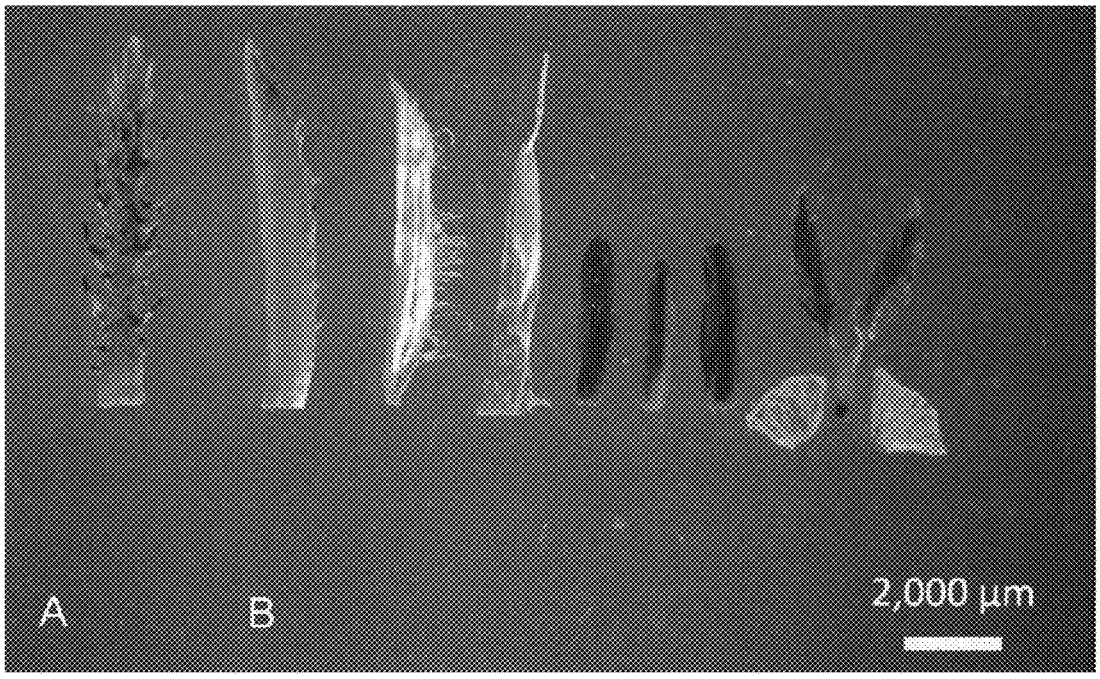
Figure 3A. Characterization of clone CIMAP-FORAGIKA: Floral Organs
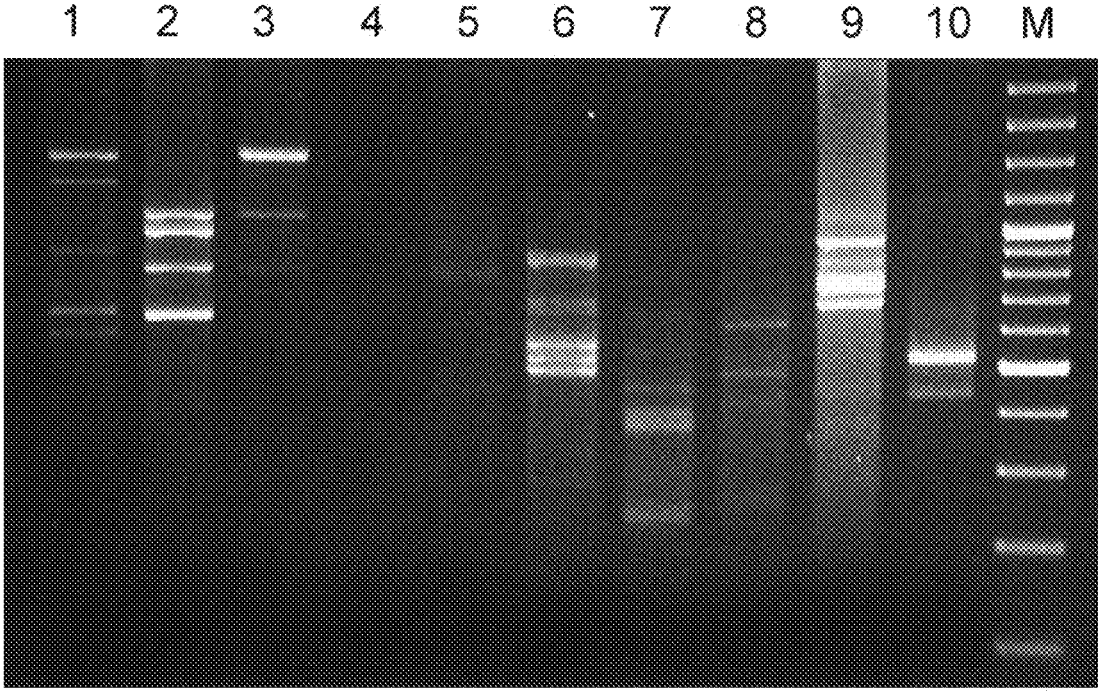
Figure 3B. Characterization of clone CIMAP-FORAGIKA: ISSR DNA finger print (M- Marker- 100 bp; and 1-10 ISSR primers)

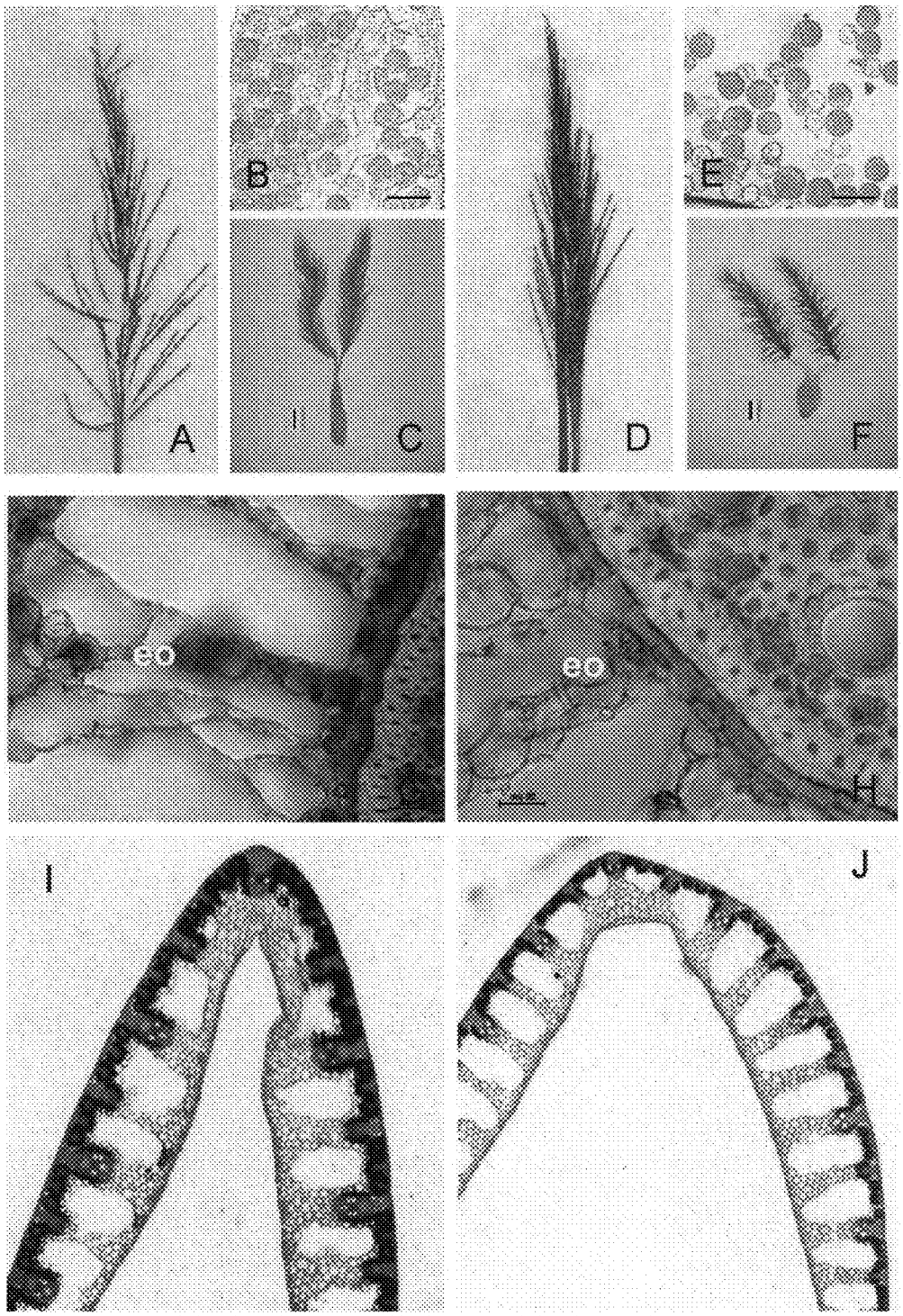
Figure 4. Depiction of micromorphological features ( Inflorescence, pollen grains, pistil, essential oil secretary cell and TS of leaf) showing comparison (eo) between Clone CIM-VRIDDHI ( A,B,C, G,I) and CIMAP-FORAGIKA (D,E,F, H, J). Note low essential oil cells, reduced leaf thickness in Clone CIMAP-FORAGIKA)